(12) United States Patent
Das et al.

(10) Patent No.: US 10,457,964 B2
(45) Date of Patent: Oct. 29, 2019

(54) METHOD FOR INCREASING THE BIOMASS SYNTHESIS CAPACITY OF A PHOTOSYNTHETIC MICROORGANISM

(71) Applicant: Reliance Industries Limited, Mumbai (IN)

(72) Inventors: Gautam Das, Adilabad (IN); Santanu Dasgupta, Mumbai (IN); Venkatesh Prasad, Bangalore (IN); Vinodhkumar Vijayakumar, Batlagundu (IN); Pranali Deore, Panvel (IN); Kannadasan Kaliyamoorthy, Tamil Nadu (IN); Sujata Kumari, Bihar (IN)

(73) Assignee: RELIANCE INDUSTRIES LIMITED, Mumbai (IN)

( * ) Notice: Subject to any disclaimer, the term of this patent is extended or adjusted under 35 U.S.C. 154(b) by 107 days.

(21) Appl. No.: 15/307,068

(22) PCT Filed: Apr. 24, 2015

(86) PCT No.: PCT/IB2015/052991
§ 371 (c)(1),
(2) Date: Oct. 27, 2016

(87) PCT Pub. No.: WO2015/166387
PCT Pub. Date: Nov. 5, 2015

(65) Prior Publication Data
US 2017/0051293 A1   Feb. 23, 2017

(30) Foreign Application Priority Data
Apr. 27, 2014   (IN) .................. 3757/MUM/2013

(51) Int. Cl.
| | |
|---|---|
| *C12N 9/96* | (2006.01) |
| *C12P 7/64* | (2006.01) |
| *C12N 15/65* | (2006.01) |
| *C12N 15/74* | (2006.01) |
| *C12N 9/10* | (2006.01) |
| *C12R 1/01* | (2006.01) |
| *C12N 1/12* | (2006.01) |
| *C12N 15/10* | (2006.01) |
| *C11C 3/00* | (2006.01) |
| *C12P 7/00* | (2006.01) |

(52) U.S. Cl.
CPC .............. *C12P 7/6463* (2013.01); *C12N 1/12* (2013.01); *C12N 9/1007* (2013.01); *C12N 9/1029* (2013.01); *C12N 15/102* (2013.01); *C12N 15/65* (2013.01); *C12N 15/74* (2013.01); *C12R 1/01* (2013.01); *C12Y 201/01037* (2013.01); *C12Y 203/01031* (2013.01); *C11C 3/00* (2013.01); *C12P 7/00* (2013.01)

(58) Field of Classification Search
None
See application file for complete search history.

(56) References Cited

U.S. PATENT DOCUMENTS

2011/0281335 A1   11/2011   Green et al.

OTHER PUBLICATIONS de Freitas et al. (Biotech. Res. & Innovation, 2017, vol. 1, pp. 14-25).*
International Search Report and Written Opinion for International Application No. PCT/IB2015/052991, dated Jul. 31, 2015, 10 pages.
Laursen, Brian Søgaard et al., "Initiation of Protein Synthesis in Bacteria", Microbiology and Molecular Biology Reviews, Mar. 2005, p. 101-123, vol. 69, No. 1, 23 pages.
Guerrero, Fernando et al., "Ethylene Synthesis and Regulated Expression of Recombinant Protein in *Synechocystis* sp. PCC 6803", Article in PLoS ONE, Nov. 2012, https://www.researchgate.net/publication/233775805, 12 pages.
Camsund, Daniel et al., "Design and characterization of molecular tools for a Synthetic Biology approach to developing cyanobacterial biotechnology", Article in Nucleic Acids Research, Mar. 2010, https://www/researchgate.net/publication/42255050, 18 pages.
Kapoor, Suman et al., "Crucial contribution of the multiple copies of the initiator tRNA genes in the fidelity of tRNA (fMet) selection of the ribosomal P-site in *Escherichia coli*", 202-212 Nucleic Acids Research, 2011, vol. 39, No. 1, doi: 10.1093/nar/gkq760, published online Aug. 26, 2010, 11 pages.

* cited by examiner

*Primary Examiner* — Hope A Robinson
(74) *Attorney, Agent, or Firm* — Westman, Champlin & Koehler, P.A.

(57) ABSTRACT

The present disclosure relates to a method for increasing biomass synthesis capacity of microorganisms. The method in accordance with the present disclosure comprises overexpressing the genes involved in protein synthesis to increase the levels of protein synthesis and thereby, increase the biomass synthesis capacity of the microorganisms. The present disclosure also provides a modified microorganism having increased biomass synthesis capacity.

7 Claims, 5 Drawing Sheets

US 10,457,964 B2

METHOD FOR INCREASING THE BIOMASS SYNTHESIS CAPACITY OF A PHOTOSYNTHETIC MICROORGANISM

CROSS-REFERENCE TO RELATED APPLICATION

This Application is a Section 371 National Stage Application of International Application No. PCT/IB2015/052991, filed 24 Apr. 2015 and published as a WO 2015/166387 A1 on 5 Nov. 2015, in English, the contents of which are hereby incorporated by reference in their entirety.

FIELD

The present disclosure relates to a method for increasing the biomass synthesis capacity of prokaryote and/or eukaryote strains and modified prokaryote and/or eukaryote strains having increased biomass synthesis capacity.

BACKGROUND

Protein biosynthesis is a necessary process in all kingdoms of life. The genetic code is decoded using complex machinery which involves several protein factors and non-coding RNA like ribosomal RNA (rRNA) and transfer RNA (tRNA). Protein length is increased by the addition of amino acids with the help of individual tRNA molecules in a sequential manner dictated by the nucleotides on the messenger RNA (mRNA).

The process of protein biosynthesis involves three distinct steps whereby mRNA is translated into a polypeptide: initiation, elongation and termination. An additional step called ribosome recycling is also involved in which the ribosomes bound to mRNA are released, split into subunits and become free to bind to new mRNA. Protein synthesis in an organism can be increased by increasing the levels of the different factors involved in the processes of initiation, elongation, termination and/or ribosome recycling.

Growth of the cells depends on the availability of proteins. Thus, increasing the availability of proteins by increasing the rates of one or more of the processes of initiation, elongation, termination, and for ribosome recycling of protein synthesis in an organism, should lead to increased growth of the organism and thereby increased biomass and overall productivity for production of desired products such as biodiesel and high value chemicals.

Various methods are known for increasing the biomass synthesis capacity of microorganisms, particularly in algae. One of the methods suggests growing the algae in the presence of growth regulators to obtain enhanced production of biomass. Another method comprises growing the algae in an alkaline pH to obtain increased algal biomass. However, the known methods are expensive and not scalable for commercial production. No attempt has been made so far to increase the biomass synthesis capacity of algae by regulating the protein synthesis mechanism i.e. increasing the protein synthesis to increase the biomass synthesis capacity of algae.

Therefore, the inventors of the present disclosure envisage a method for increasing the biomass synthesis capacity by increasing the protein synthesis capacity in microorganisms, specifically in algae and/or cyanobacteria.

The disclosure further envisages modified strains of microorganisms such as algae and/or cyanobacteria having increased biomass synthesis capacity.

OBJECTS

Some of the objects of the present disclosure which at least one embodiment is adapted to provide, are described herein below:

It is an object of the present disclosure to provide a method for overexpressing tRNA molecules to increase protein synthesis and thereby increase the biomass synthesis capacity of microorganisms.

It is another object of the present disclosure to provide a method for increasing the rate of initiation process involved in the protein synthesis to increase the levels of protein synthesis and thereby increase the biomass synthesis capacity of microorganisms.

It is another object of the present disclosure to provide a method for increasing the biomass synthesis capacity of microorganisms so as to obtain increased production of desired products.

It is still another object of the present disclosure to provide modified strains of microorganism with increased protein synthesis and thereby increased biomass synthesis capacity.

Other objects and advantages of the present disclosure will be more apparent from the following description when read in conjunction with the accompanying drawings, which is not intended to limit the scope of the present disclosure.

SUMMARY

The present disclosure in one aspect provides a method for increasing the biomass synthesis capacity of microorganisms by overexpressing the genes involved in protein synthesis. The method is characterized by the following steps: cloning at least one gene expressing initiator tRNA in a vector; introducing the vector containing the gene into the microorganism; and growing the microorganism on a medium containing a selective agent under conducive conditions and obtaining the microorganism with increased biomass synthesis capacity.

In another aspect of the present disclosure there is provided a modified strain of *Synechococcus elongatus* PCC 7942 having increased biomass synthesis capacity and having CCAP Accession Number 1479/16.

BRIEF DESCRIPTION OF THE ACCOMPANYING DRAWINGS

The method of the present disclosure will now be described with the help of the accompanying drawings, in which.

DETAILED DESCRIPTION

Some microorganisms have multiple copies of initiator tRNA in their genomes. Increased protein synthesis in these microorganisms will lead to increased biomass, which is a vital parameter for overall productivity in terms of the useful biotechnological products that can be obtained from these microorganisms such as biofuels, high value chemicals, biodiesel and so on.

It is observed that the initiator tRNA molecules or initiation factor proteins/ribosomal RNA present in the microorganisms are responsible for the initiation of the protein synthesis. It is possible to increase the amounts of the cellular initiator tRNA molecules by genetic modification of the microorganisms to have more copies of initiator tRNA molecules by altering the gene expression (up-regulating gene expression). These modified microorganisms are very useful for the production of biofuels and high value chemicals.

Thus, increasing the availability of proteins by increasing the rate of initiation of protein synthesis in the microorganisms would lead to increased growth of the microorganisms and thereby increased biomass synthesis capacity. The modified microorganisms having copies of initiator tRNA would have comparatively higher optical density (OD) than the wild type when grown under same conditions. The increased biomass synthesis capacity of the modified microorganism would therefore, result in increased production of products of interest such as biodiesel and high value chemicals.

Figure 1:
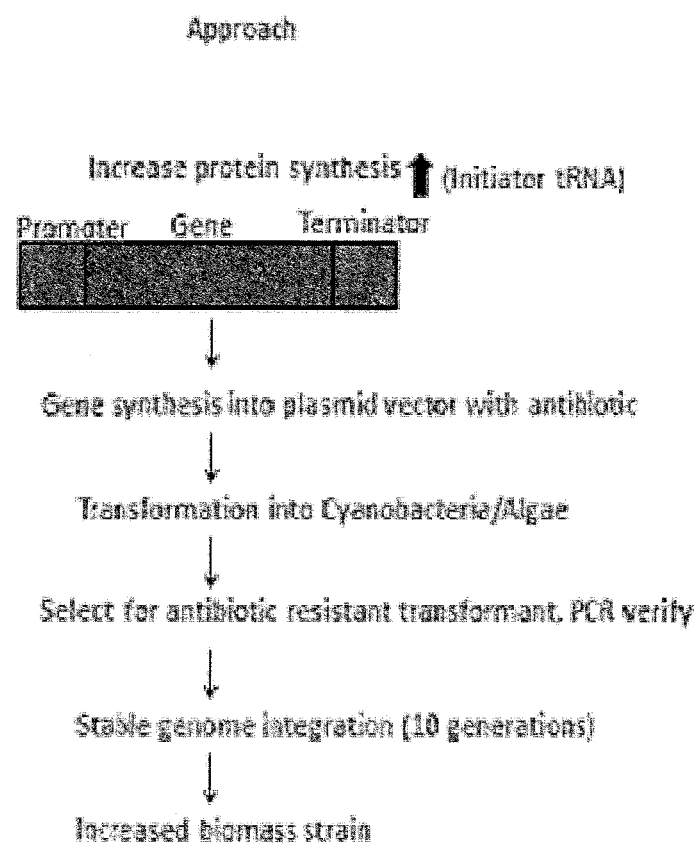
FIG. 1 illustrates a schematic process for increasing biomass synthesis capacity in microorganisms.

Therefore, in accordance with the present disclosure there is envisaged a method for increasing protein synthesis in microorganisms, specifically in algae and/or cyanobacteria (as depicted in FIG. 1).

In an aspect of the present disclosure, there is provided a method for overexpressing the different molecules involved in protein synthesis to increase protein synthesis and thereby increasing the biomass synthesis capacity of microorganisms.

The present disclosure envisages a method for increasing the protein synthesis to obtain increased overall productivity of desired products from microorganisms, specifically from algae/cyanobacteria.

In the first step, a gene involved in protein synthesis is obtained. In an embodiment of the present disclosure, the gene cloned is Initiator tRNA gene.

Next, the copies of the genes encoding for protein synthesis are cloned into a vector. In an exemplary embodiment of the present disclosure, the vector is pS1s-Ptrc.

Figure 2:
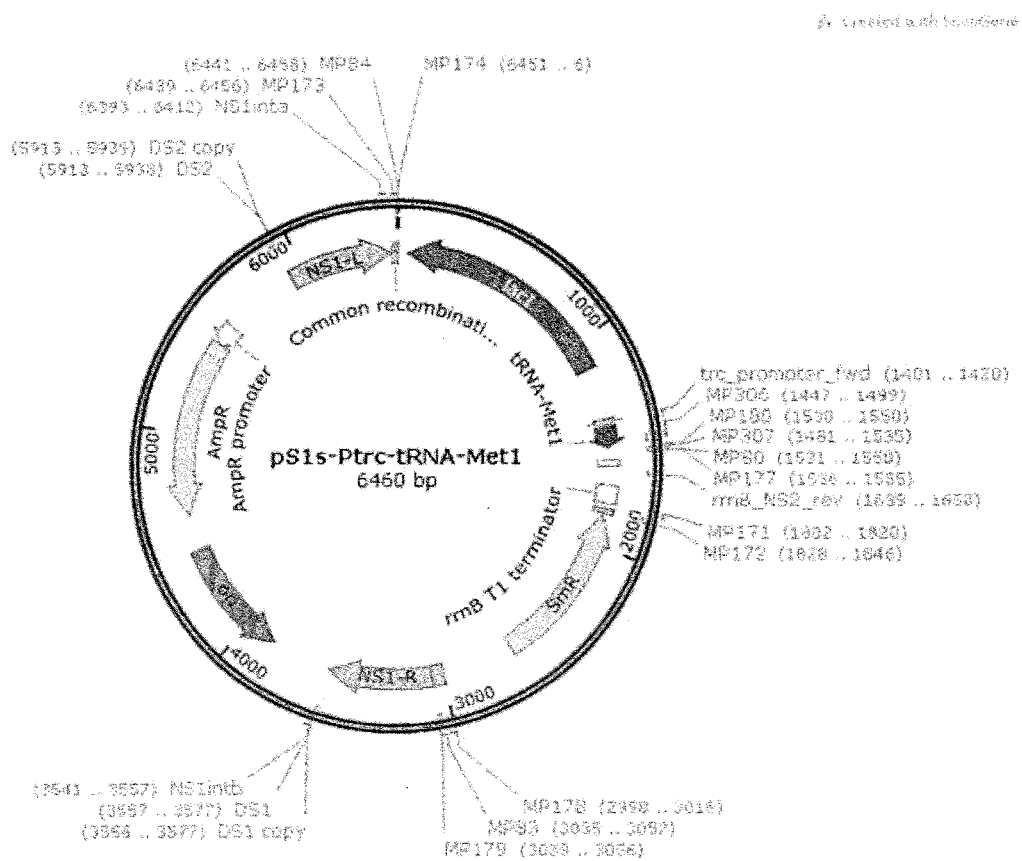
FIG. 2 illustrates the pS1s-Ptrc vector containing initiator tRNA-Met1 gene cloned into the vector.

The vector (as depicted in FIG. 2) also contains a selectable marker such as an antibiotic resistance gene. In an embodiment of the present disclosure, the antibiotic includes but is not limited to the group consisting of spectinomycin, streptomycin, ampicillin and carbenicillin.

The vector containing the gene to be overexpressed is introduced into the microorganism by direct DNA uptake method. In an embodiment of the present disclosure, the vector containing the gene to be overexpressed is introduced into the microorganism by transformation. The microorganism in accordance with the present disclosure is a photosynthetic microorganism, specifically algae and/or cyanobacteria. In an embodiment of the preset disclosure, the alga is selected from the group consisting of *Synechococcus, Chlamydomonas, Dunaliella* and *Chlorella*. In an exemplary embodiment of the present disclosure, the microorganism is *Synechococcus elongatus* PCC 7942.

The initiator tRNA in a microorganism controls the rate of initiation of protein synthesis.

In an embodiment of the present disclosure two genes encoding initiator tRNA (tRNA Met1 and tRNA Met2) from *Synechococcus elongatus* PCC 7942 are cloned separately in a vector. In an exemplary embodiment of the present disclosure the vector used is pS1S-pTrc containing antibiotic resistance genes (as depicted in FIG. 2). The vector pS1s-pTrc is used for the transformation of *Synechococcus elongatus* PCC 7942 by direct DNA uptake method. Transformation is then confirmed by PCR. The wild type and the transformants are then allowed to grow and the biomass synthesized is measured (using optical density) for comparison.

The protein synthesis in a microorganism can also be increased by overexpressing other molecules involved in the protein synthesis such as Initiation Factor-3 (IF-3) and Peptidyl-tRNA hydrolase (PTH). IF-3 in an organism controls the rate of initiation of protein synthesis. PTH controls the rate of elongation during the protein synthesis.

In accordance with another aspect of the present disclosure, there are provided modified strains of microorganisms, specifically modified strains of algae and/or cyanobacteria having increased biomass synthesis capacity, particularly, a modified strain in accordance with the present invention can be *Synechococcus elongatus* PCC 7942 deposited in the Culture Collection of Algae and Protozoa (CCAP), SAMS Limited, Scottish Marine Institute, Dunbeg, Oban, Argyll, PA37 1QA, UK and having CCAP Accession Number 1479/16.

The present disclosure is further described in light of the following laboratory experiments which are set forth for illustration purposes only and not to be construed for limiting the scope of the disclosure.

Experiment 1: Transformation of *Synechococcus elongatus* PCC 7942

Ten milliliters of inoculum containing *Synechococcus elongatus* PCC 7942 (Institut Pasteur, France) from the culture having an $OD_{750}$ of 2 was added in 40 ml of fresh BG11 (Invitrogen) media in a 100 ml Erlenmeyer flask. Ten mM sodium bicarbonate (Sigma) was added to freshly inoculated culture (1 ml was added from 0.5 M stock). The culture was incubated overnight at 30° C. on a Kuhner Shaker at 100 rpm in the presence of 2% $CO_2$.

The culture was streaked on Luria Agar (Fluka) plate and incubated at 37° C. for 24 hours to check for bacterial contamination. The plates were then incubated at room temperature for next 24 hours to check for fungal contamination. No contamination was observed on the plates.

The cells were then harvested in 50 ml falcon tube. Culture was centrifuged at 4000 rpm for 10 minutes at room temperature. The supernatant obtained was discarded. The pellet was re-suspended in 10 ml BG11 media (Invitrogen). Ten mM sodium bicarbonate (Sigma) was added (0.2 ml was added from 0.5 M stock) to the BG11 media. The culture was centrifuged at 4000 rpm for 10 minutes at room temperature. The supernatant was discarded. Pellet was re-suspended in 2.4 ml fresh BG11 media (Invitrogen). Ten mM sodium bicarbonate was added (0.048 ml was added from 0.5 M stock).

Three hundred microliters of culture were distributed in sterile 1.5 ml Eppendorf tubes. In all 8 Eppendorf tubes were prepared, each Eppendorf tube containing 300 μl of the culture. Thousand nano grams of DNA for transformation was added to the tubes. In one of the tubes the DNA was not added, which served as control for the experiment. The Eppendorf tubes were placed in 50 ml falcon tubes and wrapped with aluminum foil. The tubes were then incubated overnight at 30° C. on a Kuhner shaker at 100 rpm.

BG11 (Invitrogen) media plates containing appropriate antibiotics were prepared and the plates were dried in a biosafety cabinet for 30 minutes. The working stock of the antibiotics prepared is summarized in Table-1.

TABLE 1

Working stock of the antibiotics used

| S. No. | Antibiotic | Working Stock |
| --- | --- | --- |
| 1. | Carbenicillin (Sigma) | 50 mg/ml in sterile distilled water |
| 2. | Kanamycin (Sigma) | 50 mg/ml in sterile distilled water |
| 3. | Streptomycin (Sigma) | 50 mg/ml in sterile distilled water |

TABLE 1-continued

Working stock of the antibiotics used

| S. No. | Antibiotic | Working Stock |
| --- | --- | --- |
| 4. | Spectinomycin (Sigma) | 50 mg/ml in sterile distilled water |
| 5. | Chloramphenicol (Sigma) | 35 mg/ml in ethanol |

After completion of the incubation period, 150 µl from each tube was plated on the selection media containing the antibiotic using glass beads. Plates were incubated at room temperature, having a low light at 12 h: 12 h light: dark cycle. After incubation, tiny colonies were observed on the selection plates. One hundred and thirty colonies were patched on fresh selection plates. Four single colonies (Clone-1, Clone-2, Clone-3 and Clone-4) were used for colony PCR with Neutral Site (NS) primer to check for the integration. These NS primers once integrated do not disrupt the activity of the genome in any way.

Single colony was suspended in 50 µl of sterile distilled water and incubated at 100° C. for 15 minutes. This was used as the template for PCR. The concentration of the reagents used for PCR is summarized in Table-2.

TABLE 2

| | Working concentration | Volume (µl) |
| --- | --- | --- |
| Master Mix 2X - Sigma Taq pol. | 1× | 5 |
| Primer 10 mM stock - DSS, MP83, MP84, MP86 | 0.5 mM | 0.5 each |
| Template | >250 ng | 2 |
| DNase free water (Sigma) | — | 1 |
| Reaction volume | — | 10 |

PCR was carried out as per the temperatures given below:
1-94° C. for 5 minutes,
35-94° C. for 30 seconds, 60° C. for 30 seconds, 72° C. for 2 minutes,
1-72° C. for 5 minutes.

Figure 3:
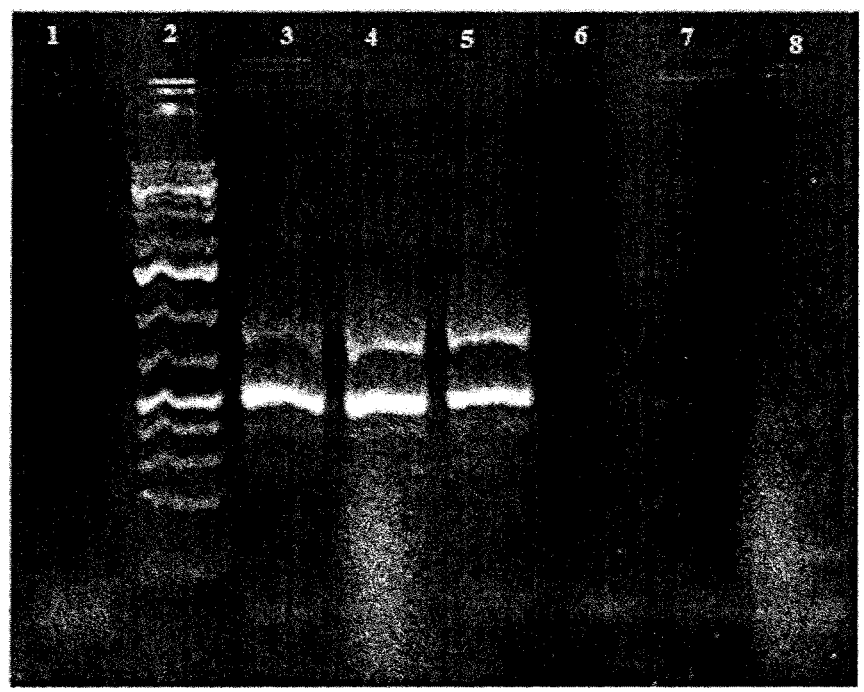
FIG. 3 illustrates the PCR amplification of the wild type *Synechococcus elongatus* PCC 7942 and the modified *Synechococcus elongatus* PCC 7942 (containing copies of genes for encoding the initiator tRNA-Met1)

The PCR amplification obtained is depicted in FIG. 3. Initiator tRNA gene was used for the transformation. From left to right, Lane-1: negative control, Lane-2: 1 kb plus ladder, Lane-3: Clone-1, Lane-4: Clone-2, Lane-5: Clone-3, Lane-6: Clone-4, Lane-7: plasmid control and Lane-8: wild type. Clone-1, Clone-2 and Clone-3 shows positive transformation and is confirmed by the presence of bands corresponding to 500 bp and 700 bp. Clone-4 was not used for further studies as the bands obtained were not prominent. The plasmid control shows no band as the DNA has been integrated into the genome of *Synechococcus elongatus* PCC 7942.

The details of the vector used in the present disclosure for biomass synthesis capacity studies are given below in Table-3.

TABLE 3

| S. No | Vector | Antibiotic Used (µg/ml) | Vector Size (bp) | Restriction digestion for confirmation |
| --- | --- | --- | --- | --- |
| 1 | pS1s-pTrc (containing initiator tRNA cloned) | Spectinomycin (SP)-2 | 6460 | Spe-I & EcoR-I HF 1487 bp |
| 2 | pS1s-pTrc | Streptomycin (SM)-2 | 6400 | Empty Vector |

Experiment 2A: Spot Assay

Single colony from 3 positive clones (Clone-1, Clone-2 and Clone-3) after three generations, and the wild type was inoculated into 500 µl of BG11 (Invitrogen)+Spectinomycin/Streptomycin (Sigma) 2 µg/ml and incubated at 30° C. with shaking and continuous light (intensity=125 µE/m$^2$/s) for 5 days. The culture was first scaled up to 5 ml, then to 50 ml with the selective media. Neat (undiluted), $10^{-1}$, $10^{-2}$, and $10^{-3}$ dilutions were used for the spot assay.

Ten microliter from each dilution was spot inoculated on 100 mM Isopropyl β-D-1-thiogalactopyranoside (IPTG) and NON-IPTG plates in duplicates and were incubated at two different temperatures of 30° C. and 37° C. for 48 hours. As a Trc-based vector is used in the present disclosure, addition of isopropyl β-D-1-thiogalactopyranoside (IPTG) leads to the induction of the Trc promoter. One mM of IPTG was used for preparing the plates for spot inoculation.

Figure 4A:
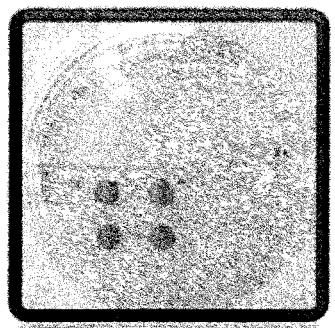
FIG. 4A illustrates the spot inoculation of the wild type and the modified *Synechococcus elongatus* PCC 7942 on NON-IPTG plate and incubated at 30° C.
Figure 4B:
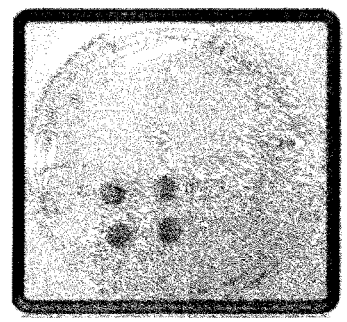
FIG. 4B illustrates the spot inoculation of the wild type and the modified *Synechococcus elongatus* PCC 7942 on IPTG plate and incubated at 30° C.
Figure 5A:
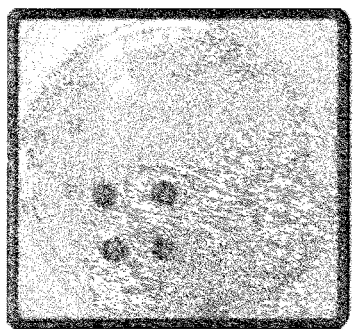
FIG. 5A illustrates the spot inoculation of the wild type and the modified *Synechococcus elongatus* PCC 7942 on NON-IPTG plate and incubated at 37° C.
Figure 5B:
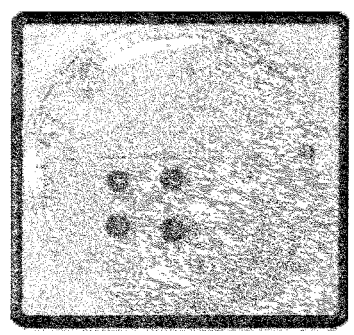
FIG. 5B illustrates the spot inoculation of the wild type and the modified *Synechococcus elongatus* PCC 7942 on IPTG plate and incubated at 37° C.

Growth of the transformants were observed in neat and $10^{-1}$ dilutions of the spot assay plates incubated at 30° C. as depicted in FIGS. 4A and 4B. Growth of the transformants were also observed in neat and $10^{-1}$ dilutions of the spot assay plates incubated at 37° C. as depicted FIGS. 5A and 5B.

Experiment 2B: Growth Curve Assay

Fresh inoculum of Clone-1 having an initial OD of 0.2-0.3 at 750 nm was inoculated into 50 ml BG11+SP/SM 2 µg/ml. The culture was incubated at two different temperatures of 30° C. and 37° C. with shaking at 100 rpm shaking and in the presence of light for 72 hours. The experiment was carried out in triplicates for both, wild type and the transformant (Clone-1).

The OD was monitored for 72 hours. Average of the triplicates was used for plotting the graphs.

Figure 6A:
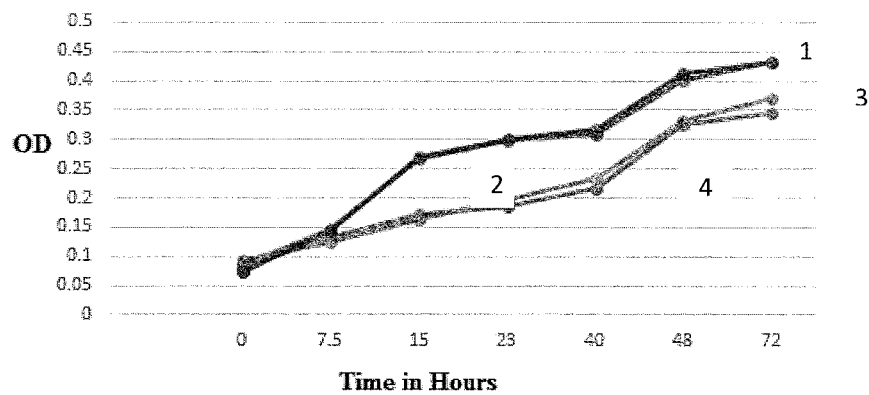
FIG. 6A illustrates the growth curve of the wild type and the modified *Synechococcus elongatus* PCC 7942 grown at 30° C.

FIG. 6A illustrates the graphical representation of the OD obtained for the wild type and Clone-1 grown at 30° C. for 72 hours. Line-4 depicts uninduced wild type and Line-3 depicts induced wild type Line-2 depicts uninduced Clone-1 and Line-1 depicts induced Clone-1.

Figure 6B:
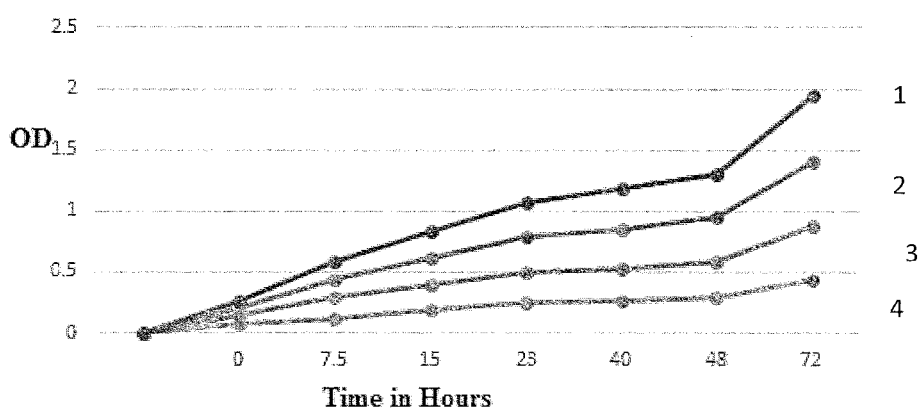
FIG. 6B illustrates the growth curve of the wild type and the modified *Synechococcus elongatus* PCC 7942 grown at 37° C.

FIG. 6B illustrates the graphical representation of the OD obtained for the wild type and Clone-1 grown at 37° C. Line-3 depicts induced wild type and Line-4 depicts uninduced wild type. Line-2 depicts uninduced Clone-1 and Line-1 depicts induced Clone-1.

It can be clearly seen from the FIGS. 6A and 6B that the transformant (Clone-1) shows higher OD as compared to the wild type and hence, higher biomass was synthesized by Clone-1 containing the initiator tRNA.

One of the major advancement of the present disclosure is the use of tRNA for increased protein synthesis resulting in enhanced biomass synthesis capacity in the transformants.

Technical Advancements

The technical advancements offered by the present disclosure are as follows:
- The present disclosure provides a method for overexpressing the different molecules involved in protein synthesis to increase protein synthesis and hence, the biomass synthesis capacity of microorganisms.
- The present disclosure provides a method for increasing the biomass synthesis capacity of microorganism to obtain increased production of desired products.
- The present disclosure provides modified microorganisms having increased biomass synthesis capacity as compared to the wild type.

The embodiments as described herein above, and various features and advantageous details thereof are explained with reference to the non-limiting embodiments in the description. Descriptions of well-known aspects, components and molecular biology techniques are omitted so as to not unnecessarily obscure the embodiments herein.

The foregoing description of specific embodiments will so fully reveal the general nature of the embodiments herein, that others can, by applying current knowledge, readily modify and/or adapt for various applications of such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein. Further, it is to be distinctly understood that the foregoing descriptive matter is to be interpreted merely as illustrative of the disclosure and not as a limitation.

Having described and illustrated the principles of the present disclosure with reference to the described embodiments, it will be recognized that the described embodiments can be modified in arrangement and detail without departing from the scope of such principles.

While considerable emphasis has been placed herein on the particular features of this disclosure, it will be appreciated that various modifications can be made, and that many changes can be made in the preferred embodiment without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

The invention claimed is:

1. A method for increasing the biomass synthesis capacity of a photosynthetic microorganism, wherein the photosynthetic microorganism is selected from the group consisting of algae and cyanobacteria, said method characterized by the following steps:
   a. cloning at least one gene expressing initiator tRNA-Met1 in a vector;
   b. introducing said vector containing said gene into said photosynthetic microorganism; and
   c. growing said microorganism on a medium containing a selective agent under conducive conditions and obtaining a photosynthetic microorganism with increased biomass synthesis capacity.

2. The method as claimed in claim 1, wherein said algae is selected from the group consisting of *Chlamydomonas, Dunaliella* and *Chlorella*.

3. The method as claimed in claim 1, wherein said selective agent is at least one antibiotic selected from the group consisting of spectinomycin, ampicillin, carbenicillin and streptomycin.

4. The method as claimed in claim 1, wherein said vector is pS1s-Ptrc.

5. The method as claimed in claim 1, wherein said photosynthetic microorganism with increased biomass synthesis capacity has higher optical density when measured at 750 nm.

6. The method as claimed in claim 1, wherein said cyanobacteria belongs to the genus *Synechococcus*.

7. The photosynthetic microorganism with increased biomass synthesis capacity, as claimed in claim 1, is *Synechococcus elongates* PCC 7942 having Accession Number 1479/16.

* * * * *